US00PP09530P

United States Patent [19]

Salas

[11] Patent Number: Plant 9,530

[45] Date of Patent: Apr. 30, 1996

[54] 'FRUTA DE ORO SEEDLESS' AVOCADO TREE

[75] Inventor: Juan A. Salas, Orotina, Costa Rica

[73] Assignee: Tropico De Oro S.A., Orotina Alajuela, Costa Rica

[21] Appl. No.: 409,853

[22] Filed: Mar. 23, 1995

[51] Int. Cl.[6] ..... A01H 5/00

[52] U.S. Cl. ..... Plt./44

[58] Field of Search ..... Plt./33.1, 44

*Primary Examiner*—James R. Feyrer
*Attorney, Agent, or Firm*—Worrel & Worrel

[57] ABSTRACT

A new and distinct variety of avocado tree which is distinguished by producing fruit which are entirely free of a pit, stone, or seed, which are mature for harvesting and shipment approximately mid May to mid July in Orotina, Alajuela, Costa Rica in Central America and which have flesh possessing an excellent flavor, a creamy smooth texture with no fiber or stringiness and which does not darken when cut open.

1 Drawing Sheet

BACKGROUND OF THE NEW VARIETY

The present invention relates to a new and distinct variety of avocado tree, which will hereinafter be denominated varietally as the 'Fruta De Oro Seedless' avocado tree, and, more particularly, to an avocado tree which produces avocados which are entirely free of pits, stones, or any other detectable seeds.

The discovery of this new variety of fruit having significant commercial potential is an event having considerable, and possibly enduring benefits in commercial markets and commercial nurseries. Such commercial markets are very receptive to new variety of this nature. One such benefit would be the seedless avocado having no loss of weight because of its seedless character. The potential for nursery stock, domestic, and commercial is excellent.

Substantial research and development has been devoted for many decades to the creation, or discovery, of commercial varieties of fruits and vegetables which have no seeds, or at least seeds few in number and of a soft and readily digestible nature. The presence of seeds, whether full size pits or stones as in the case of stone fruit, or a multiplicity of small seeds, detracts from the commercial value thereof in several respects. They are a nuisance to the consumer because, depending upon the variety of fruit or vegetable, they are wholly, or substantially, inedible and therefore must be removed prior to, or during, consumption. This process, again depending upon the variety, may be difficult to the degree that removal of the seeds is not worth the effort. In these instances, a market for these varieties of fruits or vegetables is lacking. The seeds themselves may be bitter, or otherwise have an unpleasant flavor so that the flavor of the flesh of the fruit or vegetable is contaminated thereby. In addition, such seeds interfere with, or prevent, processing of the flesh of the fruit or vegetable. The seeds may be difficult to remove, or may fragment within the flesh during commutation, or may jam mechanical equipment employed in such processing. For all of these, as well as other reasons, the development of seedless, or substantially seedless, varieties of fruits and vegetables for commercial usage has long been a focal point of research and development.

Insofar as the inventor is aware, there has not heretofore been a variety of avocado tree which produced fruit which did not have a large and very hard pit or stone. In most varieties of avocados, with exception of the occasional tiny "cocktail" or 'Lady Finger' avocado, the pit is substantially spherical, quite large in size and very hard. While in most varieties of avocado, the pit is relatively easy to remove, its presence nonetheless interferes with the commerical usage thereof in all of the ways heretofore set forth. The avocado tree of the present invention is the first known to the applicant which produces full size fruit which is completely lacking in any pit, or seed, whatsoever.

ORIGIN AND ASEXUAL REPRODUCTION OF THE NEW VARIETY

The present variety of avocado tree hereof was discovered in about 1974 by the inventor amongst mango and avocado trees on his property located in Orotina, Alajuela, Costa Rica in Central America. The parent tree of the new variety is believed to be an early sport, or chance seedling. Since the parent tree is old and no budunion is evident thereon, the origin of the parent tree is not known with certainty. The inventor continued to observe the parent tree over the succeeding years carefully noting its distinguishing characteristics. It was noted that avocados produced by the parent tree were in every case different from those of any other known variety, principally in that all fruit was seedless.

The new variety was first asexually reproduced at the direction of the inventor in 1982 by grafting bud wood onto native root stock. The inventor has observed the progeny of the parent tree through successive growing seasons thereafter and confirmed that the progeny are, in all respects, identical to the parent tree.

SUMMARY OF THE NEW VARIETY

The avocado tree of the present invention is characterized principally as to novelty by producing fruit which are entirely free of a pit, stone, or other seeds, which have a generally cucumber like shape, a butter yellow flesh coloration and which are ripe for commercial harvesting and shipment approximately May 15 to July 15 in the Orotina, Alajuela, Costa Rica in Central America. The new variety is not similar to any known avocado tree, but has an excellent flavor similar to that of the fruit of the "Fuerte" avocade tree with a nutty flavor similar to that of the fruit of the 'Hass' avocado tree. The flesh of the fruit of the new variety, at maturity, has a creamy smooth texture with no detectable fibers or stringiness.

BRIEF DESCRIPTION OF THE DRAWING

The accompany drawing is a color photograph showing the fruit of the new variety including a first in side elevation; a second of somewhat smaller size in side elevation; a third sectioned transversely thereof to expose the flesh; a fourth sectioned longitudinally thereof to expose the flesh thereof while displaying the complete absence of a pit, stone or seeds; a fifth also sectioned longitudinally thereof; and representative mature foliage and young shoots, all of the new variety of the present invention.

DETAILED DESCRIPTION

Referring more specifically to the botanical details of the new and distinct variety of avocado tree, the following has been observed under the ecological conditions prevailing in the area of origin located in Orotina, Alajuela, Costa Rica in Central America. All major color code designations are by reference to the *Dictionary of Color,* by Maerz and Paul, Second Edition, 1950. Common color designations are also occasionally employed.

TREE

Generally: The parent tree is generally old and of large size. There is no evidence of a budunion. Accordingly, the parent tree is believed to be either an early sport, or a chance seedling. The tree's age and origin are otherwise unknown. The new variety is believed to be in the genus: *Persea americana,* and probably of the subspecies "West Indian". Botanists are, however, still undecided about the many forms of avocados found in Costa Rica.

*Size.*—Large and tall. Greater than 914.4 cm (30 feet) in height.

*Vigor.*—Vigorous.

*Figure.*—Upright and tall.

*Productivity.*—Very good, up to 300 fruit per tree.

*Regularity of bearing.*—Alternate, but not to extremes. Typical for avocado trees.

Trunk:

*Size.*—Diameter — 75 cm (30 inches).

*Surface texture.*—Moderately rough.

*Color.*—Plate 7, C-5, Sultana, gray/tan.

Branches: Upright, typical of avocado.

*Size.*—Variable depending on the age of the tree.

*Surface texture.*—Smoother than trunk.

*Color.*—One year or older wood — same as trunk. Plate 7, C-5, Sultana, gray/tan.

*Color.*—Immature branches — Plate 21, L-12, Imperial Jade.

LEAVES

Size:

*Generally.*—Very large as compared with many other avocado varieties.

*Average length.*—15 cm (6 inches) to 37 cm (15 inches).

*Average width.*—12 cm (5 inches).

Shape: Obovoid.

*Tip.*—Acute, with some twisting.

*Base.*—Angular.

*Crossection.*—Incurved.

Pubescence: Moderate on under surface.

Color:

*Upwardly disposed surface.*—Plate 31, A-10, Danube Green.

*Downwardly disposed surface.*—Plate 21, B-7, Tarragon.

*Mid vein.*—Plate 19, K-10, Bud Green.

Marginal form:

*Generally.*—Smooth to very slightly wavy (more wavy with age).

Petiole:

*Size.*—N/A.

*Length.*—4 cm (1.5 inches) to 5 cm (2 inches).

*Diameter.*—0.3 cm (⅛ inch) to 0.5 cm (¼ inch).

*Color.*—Plate 19, L-12, Shamrock.

Young leaves: Plate 20, L-9, Eden Green, with some light red flecks.

FLOWERS

Flower buds:

*Size.*—¼" average.

*Surface texture.*—Wavy.

Flowers:

*Generally.*—Multiple flower inflorescences with 50 to 100 flowers each. Observations suggest that the variety is a "B" Type — female in PM, close over night, male in AM. Need more observation on viability of stigma and pollen before this determination can be confirmed.

*Date of bloom.*—Mid November to February.

*Size — Generally.*—When full blown — ⅓ ".

*Petals and sepals — Color.*—Plate 19, J-6, Apple Green.

Petiole and peduncle — Color.—Plate 19, K-10, Bud Green.

*Anther — Color.*—Plate 19, K-2, Citron Green.

FRUIT

Maturity when described: Ripe for commercial harvesting and shipment approximately Mid May to Mid July in Orotina, Alajuela, Costa Rica in Central America. May hang on tree longer, but never tested. Typically, the fruit is on the tree for six months. Fruit is set parthenocarpily, without cross pollination, and thus, no seeds are produced.

Size:

*Generally.*—Large, but with variation in sizes as evidenced in the accompanying photographic drawing.

*Typical average diameter.*—4 cm (1.5 inches) to 5 cm (2 inches).

*Smallest average diameter.*—4 cm (1.5 inches).

*Largest average diameter.*—6 cm (2.5 inches).

*Typical length.*—12 cm (5 inches) to 15 cm (6 inches).

*Smallest average length.*—10 cm (4 inches).

*Largest average length.*—20 cm (8 inches).

*Typical average weight.*—150 g (6 oz) to 250 g (9 oz).

*Smallest average weight.*—100 g (3 oz).

*Largest average weight.*—450 g (16 oz).

Shape: Cucumber shaped with slight crook in some fruits. Crossection is mostly round, with very slight ridges and flutes running with the longitudinal axis in some fruit.

Pedicel: Conical. Asymmetrical and conspicuous.

*Size — Diameter.*—0.6 cm (¼ inch).

Stem cavity:

*Generally.*—Little or no stem cavity depression.

Stem:

*Color.*—Plate 19, L-12, Shamrock.

*Size.*—Length — 7.5 cm (3 inches) to 15 cm (6 inches). Diameter — 0.6 cm (¼) inch).

Seed: None.

Seed void: Because this is a seedless variety, there is only a slight void, mainly toward dorsal end, 0.6 cm (¼ inch) to 10 cm (4 inches).

*Length.*—Mainly toward dorsal end, 0.6 cm (¼ inch) to 10 cm (4 inches).

*Diameter.*—Mainly toward dorsal end, 0.2 cm (⅛ inch) to 0.5 cm (¼ inch).

Apex:

*Shape.*—Rounded and level.

Skin:

*Thickness.*—Less than 1.0 mm (1/32 inches).

*Smoothness.*—Very smooth.

*Tendency to crack.*—None observed.

*Color.*—Range of colors, depending on size, location on tree and maturity. Does not change color when softens. Lightest — Plate 23, L-1, Holly Green. Darkest — Plate 30, D-10, Meadow Green.

Flesh: Smooth, buttery, no fiber.

*Flesh color.*—Plate 17, E-3, Butter Yellow. Unique characteristic of fruit is that it does not darken when cut open and exposed to the atmosphere.

*Fiber.*—No fiber or stringiness.

*Flavor.*—General taste is good to excellent, similar to the fruit of the 'Fuerte' avocado tree. Intermediate Sweetness, very low bitterness and high nuttiness. No spiciness or anise flavor or odor.

*Texture.*—Between watery and buttery, depending on maturity.

*Softening.*—Time at room temperatures is 2 to 3 days in Costa Rica. No experience with cold storage. Usually uniform softening, but early fruit tend to soften first at apex.

*Oil content.*—No tests. Believed to be similar to the fruit of the 'Fuerte' avocado tree.

Use: All present commercial uses.

Keeping quality: Above average shipping and shelf life.

Resistance to disease: Excellent in present environment.

Harvesting: By hand only.

Although the new variety of avocado tree possesses the described characteristics noted above as a result of the growing conditions prevailing in Orotina, Alajuela, Costa Rica, it is to be understood that variations of the usual magnitude and characteristics incident to changes in growing conditions, irrigation, fertilization, pruning, pest control, climatic variation and the like are to be expected.

Having thus described and illustrated my new variety of avocado tree, what I claim as new and desire to be secured by Plant Letters Patent is:

1. A new and distinct variety of avocado tree substantially as illustrated and described which is distinguished from all other known varieties by producing fruit which have no pit, stone, or other seeds in the flesh thereof and which are mature for commercial harvesting and shipment approximately mid May to mid July, in Orotina, Alajuela, Costa Rica in Central America.

* * * * *

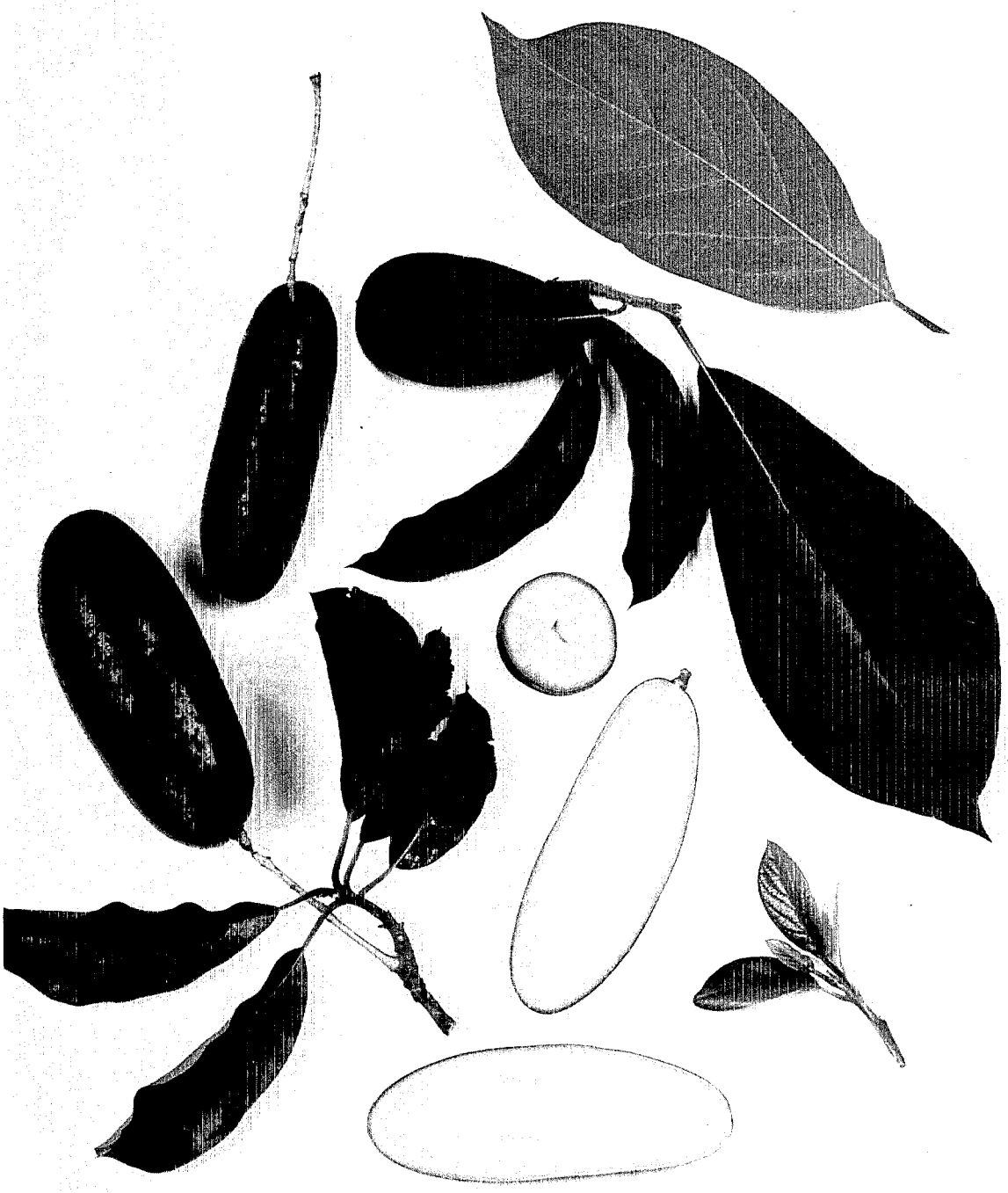

UNITED STATES PATENT AND TRADEMARK OFFICE

CERTIFICATE OF CORRECTION

PATENT NO. : Plant 9,530

DATED : April 30, 1996

INVENTOR(S) : Juan A. Salas

It is certified that error appears in the above-identified patent and that said Letters Patent is hereby corrected as shown below:

Column 4, line 15, delete "Wavy" and substitute

---Waxy---.

Signed and Sealed this

Twenty-third Day of July, 1996

Bruce Lehman

*Attest:*

BRUCE LEHMAN

*Attesting Officer*

*Commissioner of Patents and Trademarks*